United States Patent [19]

Lindstrom

[11] Patent Number: 5,010,022

[45] Date of Patent: Apr. 23, 1991

[54] METHOD FOR DETERMINING SULFUR LOADING IN ORGANIC POLYSULFIDES

[75] Inventor: Michael J. Lindstrom, Downingtown, Pa.

[73] Assignee: Atochem North America, Inc., Philadelphia, Pa.

[21] Appl. No.: 430,757

[22] Filed: Nov. 2, 1989

[51] Int. Cl.$^5$ .............................................. C01N 30/00
[52] U.S. Cl. .................................... 436/123; 436/120; 436/119; 436/161; 73/23.35; 73/23.38
[58] Field of Search ............... 436/119, 120, 123, 161, 436/30; 73/23.35, 23.38, 23.41

[56] References Cited

PUBLICATIONS

Grob, K. et al., "On-Column Injection or to Glass Capillary Columns", J. of Chromatography, 151 (1978), 311–320.
Wajon, J. E. et al., "Determination of Trace Levels of Dimethyl Polysulphides by Capillary Gas Chromatography", J. Chematography, 319 (1985), 187–194.
Szepesy, L., "Gas Chromatography", CRC Press, Cleveland, Ohio, 1970.
CA 100 (6):39664c.
*The Analytical Chemistry of Sulfur and its Compounds*, J. H. Karchmer, vol. 29, Part II, Wiley, N.Y., pp. 322–431 (1972).
*Tetrahedron*, 18, pp. 205–218 (1962).
*J. Am. Chem. Soc.*, 104, p. 6045 (1982).
Alberta Sulfur Research Ltd., *Chalktalk*, Jan. 26, 1988.
*J. Pet. Res.*, 6 (2), 153–61 (1987).
*J. Chromatogr.*, 365, 205–212 (1986).
*J. Chromatogr.*, 319 (2), 187–94 (1985).
*Am. Chem. Soc., Div. Pet. Chem.*, 28 (5), 1218–23 (1983).
*Clin. Chim. Acta.*, 130 (1), 103–10 (1983).

*Primary Examiner*—David L. Lacey
*Assistant Examiner*—David Redding
*Attorney, Agent, or Firm*—Panitch Schwarze Jacobs & Nadel

[57] ABSTRACT

A method of determining sulfur loading of an organic polysulfide composition comprises reacting the organic polysulfide composition with an organic phosphine to produce reaction products comprising organic phosphine sulfide and an organic sulfide selected from the group consisting of organic disulfide, organic trisulfide and mixtures thereof; and analyzing the reaction products by gas chromatography to determine the amount of sulfur.

16 Claims, 2 Drawing Sheets

METHOD FOR DETERMINING SULFUR LOADING IN ORGANIC POLYSULFIDES

BACKGROUND OF THE INVENTION

1. Field of the Invention

The present invention relates to a method for determining of the amount of sulfur loading in organic polysulfides.

2. Description of the Prior Art

It is known that organic disulfides react with elemental sulfur in the presence of certain catalysts to form organic polysulfides. The average number of sulfur atoms contained in the organic polysulfides is referred to as the "sulfur rank" and is determined by the amount of sulfur actually incorporated into the sulfur-laden disulfide (i.e., the polysulfide).

Recently, catalyzed dimethyldisulfide (DMDS) has become the solvent of choice for removing or preventing the formation of sulfur plugs in sour-gas wells. In fact, in certain wells, solvent must be continuously injected in order to maintain gas production. Accordingly, economics dictate that the sulfur-laden DMDS (i.e., the dimethylpolysulfide, or DMPS) be recovered, and reinjected downhole. Removal of the sulfur from the DMPS is referred to as regeneration. The extent of the sulfur loading must be quantified in order to control and monitor the regeneration process and hence, the overall operation.

Many approaches to the analysis of di- and polysulfides have been reported in the literature over the years. The *Analytical Chemistry of Sulfur and Its Compounds*, J.H. Karchmer, Vol. 29, Part II, Wiley, N.Y., pp. 322-431 (1972), provides an excellent review of these methods.

In *Tetrahedron*, 18, pp. 205-218 (1962) Moore and Trego reacted triphenylphosphine with dialkyl and diaryl tetrasulfides in benzene to obtain the corresponding disulfides. The reaction was followed by the iodometric titration of the unreacted triphenylphosphine to determine the amount of sulfur loading indirectly by titrating for the disappearance of the phosphine. While this provides the amount of sulfur loading, it does not allow the quantification of the amount of disulfide present in the sample.

The reaction of various phosphorous containing species with di- and polysulfides from the viewpoint of synthesis is known in the art. For example, see *J. Am. Chem. Soc.*, 104, p. 6045 (1982).

High pressure liquid chromatography is useful for determining polysulfide distribution in a sample of well effluent, but is fairly complicated and not suitable for field application.

A method for determining the amount of elemental sulfur present in a material suspected of containing elemental sulfur has been reported by Lesage and Clark in *Alberta Sulfur Research Ltd, Chalktalk*, Jan. 26, 1988. This method provides for the determination of elemental sulfur by reacting a sample that contains elemental sulfur with triphenylphosphine followed by quantification of the formed triphenylphosphine sulfide by gas chromatography. However, this method does not disclose the determination of sulfur loading in organic polysulfides.

Other examples of the use of gas chromatography to analyze di- or trisulfides are known in the art, e.g., *J. Pet. Res.*, 6 (2), 153-61 (1987); *J. Chromatogr.*, 365, 205-212 (1986); *J. Chromatogr.* 319 (2), 187-94 (1985); *Am. Chem. Soc., Div. Pet. Chem.*, 28 (5), 1218-23 (1983); and *Clin. Chim. Acta.*, 130 (1), 103-10 (1983).

However, analysis of polysulfides by gas chromatography has been generally limited to the analysis of polysulfides containing no more than five sulfur atoms due to the instability of higher polysulfide species toward these analytical procedures. That is, consistently accurate results in determining the sulfur rank or extent of sulfur loading in polysulfides cannot be obtained by using the prior art gas chromatographic analysis of polysulfides containing more than five sulfur atoms.

None of these references discloses a method for analysis of higher polysulfides to determine the amount of sulfur loading which may be conveniently used in the field to give consistent results.

The present invention provides an improved method for determining the extent of sulfur loading in an organic polysulfide, including higher polysulfides having more than five sulfur atoms. Moreover, the present invention allows for measurement of the total disulfide content of a given polysulfide sample, as well as of the content of impurities or additives, such as hydrocarbon solvents.

SUMMARY OF THE INVENTION

The present invention relates to a method for determining the amount of sulfur contained in an organic polysulfide composition comprising reacting a polysulfide with an organic phosphine to produce reaction products comprising an organic phosphine sulfide and an organic sulfide selected from the group consisting of an organic disulfide, an organic trisulfide and mixtures thereof; and analyzing the reaction products by gas chromatography.

BRIEF DESCRIPTION OF THE DRAWINGS

The results of gas chromatographic analysis of samples of the reaction products in accordance with the present invention are set forth in the drawings.

DETAILED DESCRIPTION OF THE INVENTION

Figure 1:
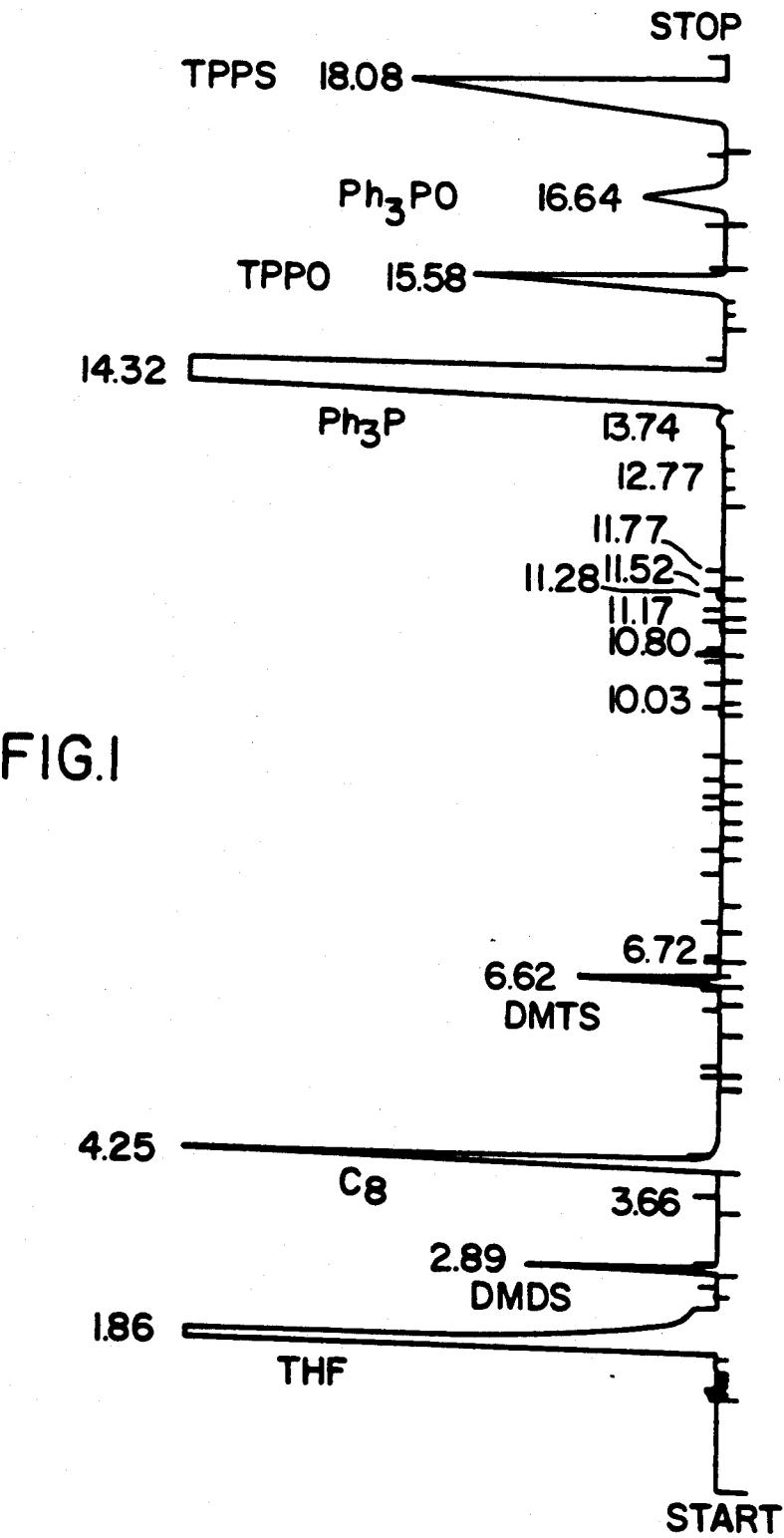
FIG. 1 is a chromatogram of an analysis of the reaction products of the reaction described in Example 1 after 5 minutes.

The present inventor has found that the method according to the present invention allows the measurement or quantification of the amount of sulfur loading in polysulfides. The present method allows for the measurement of the amount of sulfur loading for all polysulfides, including those containing more than five sulfur atoms, which cannot be analyzed by gas chromatography because such polysulfides will not elute, or are unstable to the conditions necessary for such analytical procedures.

The method according to the present invention comprises the reaction of an organic polysulfide with an organic phosphine. In this reaction, the organic polysulfide is converted to an organic disulfide, an organic trisulfide and mixtures thereof, while the phosphine is converted to a phosphine sulfide. Typically, a mixture of organic disulfide and organic trisulfide is formed. The amount of sulfur saturation of the polysulfide is then determined by gas chromatographic analysis of the reaction mixture by determining the amount of sulfur in each of the reaction products.

Generally, organic disulfides react with sulfur in the presence of certain catalysts to form organic polysulfides. Disulfides are exceptional in their ability to dissolve sulfur since the sulfur is actually chemically incorporated into the disulfide rather than being physically dissolved. The dissolution of sulfur in an organic disulfide is represented by the following reaction:

$$R^1SSR^2 + S_x \rightarrow R^1SS_xSR^2$$

wherein $R^1$ and $R^2$ may represent a number or organic radicals as defined below.

Generally, disulfides, when properly catalyzed, tend to hold extremely large amounts of sulfur due to the above-noted reaction. For this reason, catalyzed dimethyldisulfide (DMDS) has become the solvent of choice for dissolving or preventing the formation of sulfur plugs in the processing of sour-gas wells. However, during the use of DMDS in such an operation, it is necessary to quantify the amount of sulfur contained in the well effluent, i.e., the polysulfide, for effective regeneration.

The organic polysulfides which may be analyzed by the method of the present invention is limited only by the stability to the gas chromatographic conditions and associated retention times of the resulting disulfides and/or trisulfides which are formed in the reaction between the organic polysulfide and the organic phosphine.

Polysulfides suitable for the present method (and formed by the reaction noted above) may be represented by the following Formula I:

$$R^1SS_xSR^2 \qquad \text{I}$$

wherein $R^1$ and $R^2$ independently represent an alkyl group of 1 to 25 carbons; an aryl group of 6 to 25 carbons; an alkaryl group of 7 to 26 carbons; a hydroxy group; or an alkoxy alkyl group of 2 to 25 carbons and x is an integer from about 1 to 15. The value of x represents the average number of internal sulfurs in a given organic polysulfide composition, and not the maximum number of sulfurs for any one species. Preferably, $R^1$ and $R^2$ independently represent an alkyl group of 1 to 5 carbons; an aryl group of 6 to 10 carbons; an alkaryl group of 7 to 12 carbons; a hydroxy group or an alkoxy alkyl group of 1 to 5 carbons and x is an integer of from about 1 to 10. More preferably, $R^1$ and $R^2$ independently represent a methyl group.

The organic polysulfide to be analyzed for sulfur loading according to the present invention is reacted with an organic phosphine to produce, as reaction products, the corresponding organic disulfide and/or organic trisulfide, organic phosphine sulfide and other by-products which are readily analyzable by gas chromatography.

The organic phosphines suitable for use in the present method may be represented by the following formula II:

$$R^3R^4R^5P \qquad \text{II}$$

wherein $R^3$, $R^4$ and $R^5$ independently represent an alkyl group of 1 to 10 carbons, an aryl group of 6 to 25 carbons, an alkaryl group of 7 to 26 carbons, a hydroxy group or an alkoxy alkyl group of 2 to 25 carbons. Preferably, $R^3$, $R^4$ and $R^5$ independently represent an alkyl group of 1 to 5 carbons, an aryl group of 6 to 10 carbons, an alkaryl group of 7 to 12 carbons, a hydroxy group or an alkoxy alkyl group of 2 to 10 carbons. More preferably, $R^3$, $R^4$ and $R^5$ independently represent phenyl groups.

Care must be taken in choosing organic phosphines which are stable and do not substantially react with the disulfides. For example, aminophosphines, such as hexaethylphosphorous triamide and phosphites like tributyl phosphite, are not suitable for use in the present method, since they react with disulfides and have a very limited air stability.

The complete reaction between the organic polysulfide and the organic phosphine according to the method of the present invention can be represented as follows:

$$R^1SS_xSR^2 + \text{excess } R^3R^4R^5P \rightarrow R^1SSR^2 + xR^3R^4R^5PS$$

wherein $R^1$, $R^2$, $R^3$, $R^4$, $R^5$ defined above. As can be seen, the organic polysulfide has been converted to an organic disulfide and the phosphine has been converted to a phosphine sulfide. This reaction mixture is then analyzed by gas chromatographic analysis to determine the amount of sulfur loading.

In the reaction set forth above, there has been a complete conversion of the polysulfide to the disulfide. This generally requires long reaction times between the polysulfide and the phosphine treating solution, e.g., one or two days.

For more convenient reaction times of about 5 minutes to about several hours, and preferably, about 30 minutes, the reaction may be more accurately represented by the following:

$$nR^1SS_xSR^2 + nxR^3R^4R^5P \rightarrow mR^1SSR^2 + [mx+(n-m)(x-1)]R^1SSSR^2 + (x-1)R^3R^4R^5PS$$

wherein $R^1$, $R^2$, $R^3$, $R^4$, $R^5$ and x are as defined above, m is a fraction or an integer which represents the extent of conversion of polysulfide and n is any integer or a fraction thereof, which represents the amount of excess phosphine. In this case, the sulfur removal from the polysulfide is incomplete. Therefore, in performing the sulfur loading calculations, both the sulfur contained in the phosphine sulfide and the trisulfide must be considered along with the sulfur in the disulfide.

In the method according to the present invention, a weighed sample of organic polysulfide is combined with a treating solution containing an organic phosphine. The amount of the polysulfide used as a sample is preferably from about 20 to about 50 mg.

The concentration of the phosphine in the treating solution may vary depending on the sample size. However, it is preferred that the treating solution contain a two-fold molar excess of the phosphine in relation to the anticipated amount of sulfur in the polysulfide being analyzed. This is desired so that a sufficient amount of phosphine is used to provide a complete reaction. The two-fold molar excess of phosphine may be determined in practice by estimating the amount of sulfur in the solvent, determining the corresponding number of moles of sulfur and doubling this figure.

The preferred concentration of phosphine in the treating solution is from about 0.25 to about 0.5 g/cc for samples of well effluent of about 20 to about 50 mg.

Suitable solvents for use in the treating solution are saturated hydrocarbons, such as hexane; aromatics, such as toluene; and ethers, such as dioxane or tetrahydrofuran. Solvents which are known to undergo reaction with phosphines, such as chlorinated hydrocarbons and ketones, are not suitable for use as the solvent for the treating solution of the present method. Generally, a solvent is chosen in which the phosphine and phosphine sulfide are soluble within the concentration ranges utilized. The preferred solvent for use in the treating solution of the present method is tetrahydrofuran.

In addition to the phosphine, the treating solution used in the present method may also contain at least one, and preferably two internal standards for gas chromatographic determinations, which are inert to the analytical conditions used and the other reactants being employed. For example, long chain hydrocarbons or aromatics are suitable as one of the internal standards. When analyzing dimethyldisulfides, octane is the preferred internal standard. However, any conventional standards may be used which have the retention and elution times required.

It is also convenient and effective for the treating solution to comprise a second internal standard having a retention time similar to that of the formed phosphine sulfide. For example, when the phosphine formed is a triphenylphosphine sulfide, triphenylphosphate is the preferred second internal standard.

The mixture of polysulfide sample and phosphine-treating solution should be agitated to obtain a homogeneous mixture. The polysulfide/phosphine combination is allowed to stand for a period of from about 5 minutes to several hours. Preferably, the solution is allowed to stand for about 5 minutes to one hour, and most preferably, for about 30 minutes.

The end point of the reaction between the polysulfide and the organic phosphine may be determined by gas chromatography. For example, the mixture may be continuously analyzed by gas chromatography (i.e., at regular intervals) until the amount of sulfur determined remains constant.

Once the end point of the reaction is reached, the solution containing the resulting organic phosphine sulfide and the organic trisulfide is then analyzed directly by gas chromatography to determine the amount of sulfur loading.

The process of the present invention will now be illustrated in more detail by reference to the following specific, non-limiting examples.

In the following examples, the extent of sulfur loading is defined as the ratio of the weight of sulfur added to the weight of sulfur solvent (disulfide and impurities, such as diesel oil). For example, 4 grams of sulfur dissolved in 10 grams of solvent would thus be defined as 40% sulfur loading.

The instrumentation and analytical conditions used in the present examples are as set forth below.

A Hewlett-Packard Model No. 5890 gas chromatograph was used in conjunction with a Model No. 3390A integrator. The instrument is equipped for capillary columns. A flame ionization detector was also used. As the analytical column, a widebore (0.53 mm), 30 meter fused silica capillary column was used. The remainder of the analytical conditions were as follows:

a. Oven Program: 4 min @60° C., ramp 25° C./min to 280° C.
b. Injector Temperature: 325° C.
c. Detector Temperature: 325° C.
d. Column Head Pressure: 32 kPa
e. Septum Purge Vent Flow: 4.0 mL/min
f. Split Vent Flow: 87 mL/min
g. Injection: 0.1 uL sample size, purge vent off, purge delay = 1 min

EXAMPLE 1

A 40% loaded dimethyl solution was prepared through the addition of 4.0 g of sulfur to 10.0 g dimethyldisulfide (DMDS). Three drops of Jeffamine ® ED-600 were added to the DMDS. The mixture of the sulfur and the DMDS was stirred until the sulfur was completely dissolved.

In a 1-dram gc vial, 25-35 mg of the prepared polysulfide was weighed. To this was added 1 mL of a stock phosphine treating solution, containing the following concentration of components in tetrahydrofuran:

0.0178 g/cc Octane (C8);
0.28 g/cc Triphenylphosphine (TPP); and
0.0213 g/cc Triphenylphosphate (TPPO)

This mixture was then gently agitated. After 5 and 30 minutes, the reaction mixture was subjected to gas chromatographic analysis under the conditions set forth above. The results are summarized in Table I. The chromatogram of FIG. 1 resulted from the analysis of the same 5 minutes after mixing the polysulfide and phosphine solutions.

The percentage of sulfur loading, the percentage dimethyldisulfide (DMDS) present and the percentage of diesel were calculated by the computations set forth below, by comparison of the respective peak areas with the internal standards and application of the appropriate response factors.

| | Calculations for % S-Loading % DMDS and % Diesel |
|---|---|
| % S-Loading | = (wt. total S/ wt. solvent) × 100 |
| % DMDS | = ([wt. DMDS + 0.746(wt./ DMTS)]/wt. sample) × 100 |
| % Diesel | = ([wt. sample − (wt. DMDS + wt. total S)]/wt. sample) × 100 |
| wt. total S | = (wt. TPPS × 32/294) + 0.254(wt. DMDS) |
| wt. solvent | = sample wt. − wt. total S |
| wt. DMDS | = (area DMDS × wt. C8 × 4.06)/area C8 |
| wt. DMTS | = (area DMTS × wt. C8 × 5.1)/area C8 |
| wt. TPPS | = (area TPPS × wt. TPPO × 0.948)/area TPPO |

EXAMPLE 2

The procedure of Example 1 was repeated on an 80% loaded sample of dimethylpolysulfide. The results are summarized in Table 1.

EXAMPLE 3

The procedure of Example 1 was repeated on a 120% loaded sample of dimethylpolysulfide. The results are summarized in Table 1.

EXAMPLE 4

Figure 2:
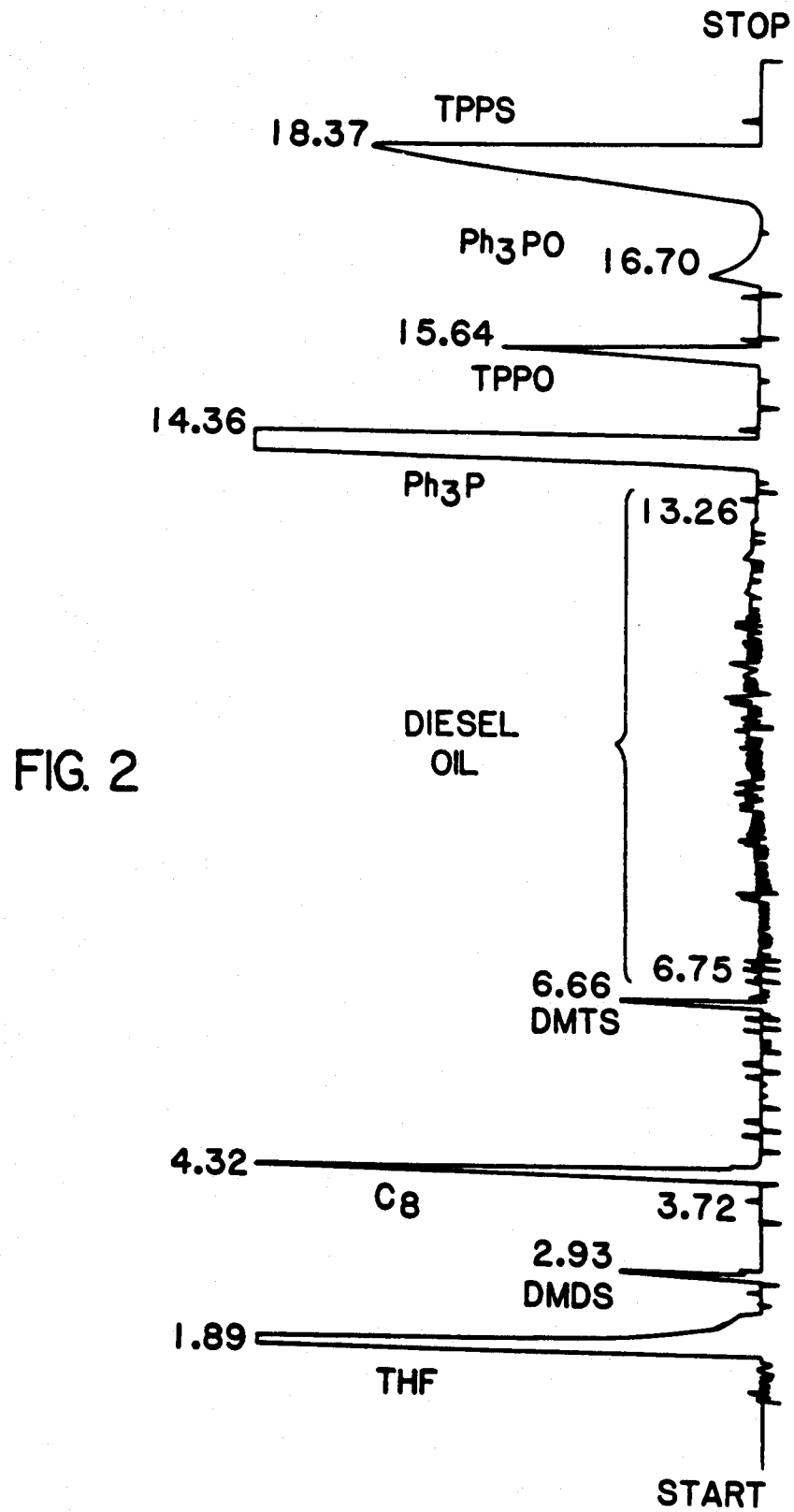
FIG. 2 is a chromatogram of an analysis of the reaction products of the reaction described in Example 4.

The procedure of Example 1 was repeated on a mixture of 42.6 wt. % of diesel oil and 57.4 wt. % of 80% loaded dimethylpolysulfide. The results are summarized in Table 1 and the chromatograpm relating to this mixture is shown at FIG. 2.

TABLE 1

% Sulfur Loading, % DMDS and % Diesel Determinations on Various Dimethyl Polysulfides

| Example | Actual S LOAD | Actual % DMDS | Actual % Diesel | Reaction Time (min) | Found S LOAD | Found % DMDS | Found % Diesel |
|---|---|---|---|---|---|---|---|
| 1 | 40 | 71.4 | — | 5 | 41.6 | 72.8 | — |
|   |    |      |   | 30 | 42.6 | 74.1 | — |
| 2 | 80 | 55.6 | — | 5 | 80.5 | 57.2 | — |
|   |    |      |   | 30 | 79.9 | 57.5 | — |
| 3 | 120 | 45.4 | — | 5 | 116.5 | 47.9 | — |
|   |     |      |   | 30 | 119.5 | 47.8 | — |
| 4 | 34.2 | 31.9 | 42.6 | 5 | 34.9 | 32.5 | 41.6 |
|   |      |      |      | 30 | 34.4 | 32.6 | 41.8 |

As can be seen from Table 1, the present process provides a sufficiently accurate determination of the sulfur-loading in a polysulfide solution. The sulfur content of the prepared sulfur-loaded solutions correlated well with the sulfur load found by gas chromatographic analysis.

The present invention may be embodied in other specific forms without departing from the spirit or essential attributes thereof and, accordingly, reference should be made to the appended claims, rather than to the foregoing specification as indicating the scope of the invention.

I claim:

1. A method of determining sulfur loading of an organic polysulfide composition comprising a polysulfide having more than 5 sulfur atoms, comprising reacting the organic polysulfide composition with an organic phosphine to produce reaction products comprising organic phosphine sulfide and an organic sulfide selected from the group consisting of organic disulfide, organic trisulfide and mixtures thereof, and quantitatively analyzing the reaction products by gas chromatography to determine the amounts of sulfur.

2. A method according to claim 1, wherein the organic polysulfide is represented by Formula I $$R^1SS_xSR^2 \quad (I)$$

wherein $R^1$ and $R^2$ independently represent an alkly group of 1 to 25 carbons; an aryl group of 6 to 25 carbons; an alkaryl group of 7 to 26 carbons; a hydroxy group, or an alkoxy alkyl group of 2 to 25 carbons; and x is an integer of from about 4 to 15; and the organic phosphine is represented by Formula II:

$$R^3R^4R^5P \quad (II)$$

wherein $R^3$, $R^4$ and $R^5$ independently represent an alkyl group of 1 to 10 carbons, an aryl group of 6 to 25 carbons, an alkaryl group of 7 to 26 carbons, a hydroxy group, or an alkoxy alkyl group of 2 to 25 carbons.

3. A method according to claim 2, wherein $R^1$ and $R^2$ each represents an alkyl group of 1 to 5 carbons, an aryl group of 6 to 10 carbons, an alkaryl group of 7 to 12 carbons, a hydroxy group, or an alkoxy alkyl group of 1 to 5 carbons; x is an integer of from 4 to 10; and $R^3$, $R^4$ and $R^5$ each represents an alkyl group of 1 to 5 carbons, an aryl group of 6 to 10 carbons, an alkaryl group of 7 to 12 carbons, a hydroxy group, or an alkoxy alkyl group of 2 to 10 carbons.

4. A method according to claim 3, wherein $R^1$ and $R^2$ each represents methyl groups; $R^3$, $R^4$ and $R^5$ each represents phenyl groups, and x is an integer of from 4 to 10.

5. A method according to claim 1, further comprising adding to the reaction products a first gas chromatogrphic internal standard.

6. A method according to claim 5, wherein the first gas chromatogrphic internal standard is selected from the group consisting of a long chain hydrocarbon and an aromatic compound.

7. A method according to claim 6, wherein the standard is the long chain hydrocarbon, wherein the long chain hydrocarbon is octane.

8. A method according to claim 5, further comprising adding to the reaction products a second gas chromatogrphic internal standard.

9. A method according to claim 8, wherein the second gas chromatographic internal standard has a retention time approximately the same as that of the formed organic phosphine sulfide.

10. A method according to claim 9, wherein the second gas chromatographic internal standard is triphenylphosphate.

11. A method according to claim 1, further comprising reacting the organic polysulfide and the organic phosphine in the presence of an inert solvent selected from the group consisting of hexane, toluene, dioxane and tetrahydrofuran.

12. A method according to claim 1, wherein a twofold molar excess of an organic phosphine is reacted with the organic polysulfide, in relation to the expected sulfur amount of the organic polysulfide.

13. A method according to claim 1, wherein the organic polysulfide is reacted with the organic phosphine for about 5 minutes to about 30 minutes.

14. A method for determining the amount of sulfur contained in a dimethylpolysulfide composition having more than 5 sulfur atoms, comprising combining the dimethylpolysulfide composition with a treating solution comprising triphenylphosphine, tetrahydrofuran, octane and triphenylphosphate; allowing the combination to stand for a period of time sufficient to allow the dimethypolysulfide and the triphenylphosphine to react; and analyzing the combination by gas chromatography.

15. A method according to claim 14, wherein the dimethylpolysulfide contained in the composition is from about 20 to 50 mg.

16. A method according to claim 14, wherein the treating solution comprises 0.25 to 0.5 grams/cc of triphenylphosphine.

* * * * *